United States Patent [19]

Payne

[11] 4,258,073

[45] Mar. 24, 1981

[54] TAKING OF FINGER PRINTS

[76] Inventor: John M. Payne, 36A High St., Maxey, Peterborough, England

[21] Appl. No.: 16,019

[22] Filed: Feb. 28, 1979

[30] Foreign Application Priority Data

Mar. 2, 1978 [GB] United Kingdom ............... 8239/78

[51] Int. Cl.³ ............................................. A61B 5/10
[52] U.S. Cl. ........................................ 427/1; 427/7; 427/13; 427/14.1; 427/27; 427/145; 427/155; 427/167; 427/421; 427/430.1; 430/48; 430/55; 430/117; 430/121
[58] Field of Search .................... 427/1, 17, 19, 24, 16, 427/7, 430.1, 145, 146, 197, 421, 154, 155, 13, 14.1, 27; 96/1 SD, 1 LY; 430/48, 55, 117, 121

[56] References Cited

U.S. PATENT DOCUMENTS

| | | | |
|---|---|---|---|
| 2,986,831 | 6/1961 | Terck et al. | 427/1 |
| 3,010,842 | 11/1961 | Ricker | 96/1 LY |
| 3,408,217 | 10/1968 | Obuchi | 427/1 |
| 3,492,140 | 1/1970 | Honjo | 427/1 |
| 3,549,253 | 12/1970 | Brodie | 427/1 |
| 3,549,397 | 12/1970 | McDonald et al. | 427/1 |

FOREIGN PATENT DOCUMENTS

| | | | |
|---|---|---|---|
| 43-21500 | 9/1968 | Japan | 427/1 |

*Primary Examiner*—Ronald H. Smith
*Assistant Examiner*—Janyce A. Bell
*Attorney, Agent, or Firm*—Donald K. Wedding

[57] ABSTRACT

A first method of revealing a fingerprint involves the charging of the surface bearing the fingerprint to a high electric potential and applying finely divided carbon to the charged surface to form a pattern thereon corresponding to the fingerprint.

The finely divided carbon may be dusted or sprayed on or may be in suspension in a dielectric liquid into which the charged surface is introduced.

In another method the surface is charged while submerged in the dielectric liquid, under the action of an electric field in the dielectric.

In another method an electrically charged sheet is brought into contact with a surface bearing a fingerprint and after being removed, the charged sheet has applied to its surface finely divided carbon which adheres thereto depending on the charge pattern remaining thereon after contact with the fingerprint.

The pattern of finely divided carbon can be fixed in position by applying thereover a transparent protective layer.

9 Claims, No Drawings

TAKING OF FINGER PRINTS

FIELD OF THE INVENTION

This invention concerns fingerprinting techniques and in particular improved methods for rendering visible fingerprints contained on surfaces from which hitherto it has been considered impossible to obtain fingerprint information.

BACKGROUND TO THE INVENTION

The most common fingerprinting techniques involve the use of fingerprint dusting powders such as graphite powder or zinc powder etc., which is dusted on to the suspect surface using a brush. The powder adheres to any deposits of skin secretions which if resulting from a fingerprint will be in the form of a unique pattern. The powdered representation so obtained can be subsequently lifted by applying to it the sticky side of an adhesive-backed transparent sheet which allows the powdered representation of the print to be lifted for further examination for example at a forensic laboratory and can subsequently be used as evidence in a court of law.

One of the disadvantages of this method is that fingerprints which are more than a few hours old cease to respond to powder treatment. It is believed that the secretions from the skin which adhere to the surface of the member on which the finger or thumb has been placed dry up or otherwise react with the surface or the atmosphere and once this so-called drying up process has been completed there has hitherto been no method of obtaining from the surface any information relating to the fingerprint.

Another disadvantage is that the dusting/powder method cannot be used on certain materials such as polythene and similar plastic sheet materials which apparently exhibit an attraction or stickiness which overrides the secretions from a fingerprint and render it virtually impossible to detect a fingerprint on such a surface. This is of significance in drug offences since most drugs are contained in polythene bags and the use of conventional powder dusting techniques for fingerprinting the drug bags have proved totally ineffective.

It is also a disadvantage of the known method (i.e. the so-called dusting technique) that the method is ineffective for removing fingerprints from the human skin. Were it to be possible to obtain fingerprint information from the skin of rape cases, assult cases and the like, additional very strong evidence could be adduced in such cases for ensuring that only the guilty person was convicted.

OBJECT OF THE INVENTION

It is an object of the present invention to provide an improved method for rendering visible a fingerprint contained on an area.

THE INVENTION

According to one aspect of the present invention a method of rendering visible a fingerprint contained on an area comprises the stage of:
(1) covering the area with a sensitized surface capable of retaining an electrostatic charge,
(2) firmly pressing the sensitized surface into contact with the said area,
(3) separating the sensitized surface from the said area,
(4) subjecting the sensitized surface to an electrostatic field so as to impart an electrostatic charge thereover which will be less in areas bearing skin secretions and the like of the fingerprint,
(5) removing the electrostatic field, and
(6) applying to the sensitized surface a finely divided particulate material so that the particles adhere to strongly charged regions of the surface but areas having little or no charge are substantially uncoated by the particles thereby to produce a pattern corresponding to the fingerprint.

The particles are preferably of a colour which is in contrast to the colour of the said surface and typically a fine black powder is used.

The particles may be finely divided carbon or a resin based pigment.

It is found that if a fingerprint exists on the area as a result of a finger or thumb having been pressed there against a pattern of charge-inhibiting lines of the skin secretion forming the fingerprint is transferred to the said surface so that when the latter is subjected to the electrostatic field a charge pattern is formed on the said surface corresponding to the lines and spaces forming the unique surface skin pattern of the finger or thumb concerned.

The particles may be in the form of a dry powder or in suspension in a dielectric liquid which will evaporate quickly at room temperature. One commercially available liquid suspension which may be used is a suspension of toner as used in certain electrostatic photocopying machines.

The pattern of particles so obtained can be photographed or lifted using adhesive-backed sheet material or tape. Where the particulate material is in suspension in a liquid which will evaporate quickly at room temperatures, time must of course be allowed for the liquid to evaporate before the adhesive-backed tape is applied.

It is preferred to use a dielectric paper i.e. capable of retaining an electrostatic charge but which is not sensitive to light. ZnO paper can be used but is obviously not as convenient as it has to be used in darkness.

The electric charge applied to the said surface may be positive or negative, depending on the materials used.

Preferably the rear of a member bearing the sensitized surface is earthed whilst the electrostatic field is applied thereto.

Preferably the means for establishing the electrostatic field is a point or wire electrode connected to one terminal of a high voltage source so as to produce a corona discharge from the electrode.

Preferably the voltage of the source is adjustable.

Where the said area is substantially flat the sensitized surface may comprise a photo-receptive film applied to one side of a flexible sheet of paper or plastics material.

One commercially available product which has been found to be satisfactory is dielectric photocopying paper.

Where the said area is undulating and irregular the surface is preferably formed on a material which can more readily be moulded over the undulations etc. than is possible with paper, so as to follow every hollow or crater in the area.

According to another aspect of the present invention a method of rendering visible a fingerprint contained on an area of a device which is portable and will support at least temporarily an electric charge comprises the steps of:
(1) subjecting the said area to an electrostatic field so as to impart an electrostatic charge thereon,
(2) immersing the said area in a bath containing a suspension of particles in a dielectric liquid, and causing a migration of the particles to the said area,
(3) removing the said area from the bath,
(4) permitting the liquid to evaporate and leave the particles behind so as to reveal any fingerprints on the area.

The patterns of particles can be rendered relatively permanent by lifting the pattern of particles using a sheet of adhesive-backed tape or sheet material, or covering the area containing the pattern with transparent adhesive-backed material or a coating of clear varnish.

According to a further aspect of the present invention a method of rendering visible a fingerprint contained on an area of a member which is portable and will support at least temporarily an electric charge comprises the steps of:
(1) immersing the member in a suspension of a finely divided particulate material in a dielectric liquid
(2) establishing an electric field in the dielectric thereby causing particles in the suspension to migrate in the direction of the immersed member the particles forming visible patterns thereon corresponding to any fingerprints on the said area, and
(3) removing the member from the dielectric liquid.

The fingerprint may be rendered permanent by allowing the liquid to evaporate and thereafter fixing the particles in place by firming them over a transparent film of a suitable quick drying substance or by securing them over a transparent layer of sheet material or lifting therefrom the particle pattern using adhesive-backed sheet material.

According to a still further aspect of the present invention a method of rendering visible a fingerprint contained on an area of a member which will at least temporarily support an electric charge, comprises the steps of:
(1) subjecting at least the said area of the member to an electrostatic field so as to impart a charge thereto, and
(2) applying finely divided particulate material to the area which has been electrically charged, and forming there a pattern of the particulate material corresponding to any fingerprint thereon.

The particulate material may be poured over the charged area or brushed or sprayed thereon. A convenient form of spray is a so-called aerosol.

The pattern of particulate material may be lifted from the area by using an adhesive backed sheet or tape material, or may be fixed in place by covering with a transparent sheet or a layer of clear varnish or the like, sprayed thereover.

The invention has been used to render visible fingerprints on the skin and on plastics materials such as plastic bags and the like.

The invention will now be described with reference to a number of specific examples.

EXAMPLE 1

An area of skin believed to contain a fingerprint is first covered by a sheet of flexible material capable of retaining an electrostatic charge e.g. dielectric paper as used in photocopying, with the coated side in contact with the skin to be checked. The flexible material is then lightly but firmly pressed over the skin so as to make good contact therewith. The mineral coating of the dielectric paper will absorb the skin secretions of the fingerprint.

After removing the flexible sheet material from the skin, the coated surface thereof is charged electrostatically typically by bringing it into close proximity to an electrode charged to a live voltage (typically a few thousand volts).

After charging the coated surface, finely divided carbon powder is applied to the charged surface. This may be done by dusting or by spraying or brushing or immersing the dielectric sheet in a bath containing the powder either in a dry form or in suspension in a liquid which will evaporate quickly at room temperature.

The carbon powder will be found to adhere to the charged surface in a pattern corresponding to any fingerprint or fingerprints on the skin area into which the zinc oxide surface was brought into contact. The absorbed fingerprint secretions will effectively inhibit the charge in the area of the secretions.

By spraying on a quick drying clear varnish or similar, the powder pattern of the fingerprint can be rendered permanent.

Alternatively, the powder pattern may be lifted by laying thereon a sheet of tape having an adhesive backing so as to cause the carbon powder to cling thereto. Subsequently peeling off the adhesive backed material will cause the pattern of powder to be largely removed, intact, still clining to the adhesive. This can then be trapped by applying a second sheet of material, also preferably adhesive backed, to the powdered adhesive layer on the first mentioned sheet or tape. Where the second sheet is adhesive backed it is preferably applied to the first mentioned sheet with the two adhesive surfaces together. The powder pattern is then trapped therebetween.

At least one of the two sheets/tapes should be transparent and a useful construction is one piece which is transparent and one which is either opaque and white or light coloured or white and translucent.

EXAMPLE II

A plastic bag (e.g. a polythene bag) which is believed to bear one or more fingerprints may be tested as follows:

The bag is first charged electrostatically by bringing it into close proximity to a high voltage electrode.

The charged bag is then immersed in a bath containing a suspension of finely divided carbon powder in a dielectric liquid which evaporates quickly at room temperature.

After immersion for a few seconds the bag is carefully removed and hung up to dry.

It will be found on inspection that any fingerprints on the bag will appear as a pattern of clear, transparent lines in the otherwise generally black coating on the bag.

The pattern can be rendered relatively permanent by covering it with a sheet of adhesive backed material, preferably transparent sheet material, or spraying on a clear varnish. If the adhesive backed material is peeled off, the pattern will also be found to cling thereto and can be sealed by applying a second sheet of material to the sticky side of the adhesive backed material.

EXAMPLE III

Where the subject on which the fingerprint is believed to be located is not suitable for immersion in a bath of liquid, as in Example II an alternative procedure may be adopted. In this third process the immersion step is replaced by a step of spraying or dusting dry powder onto the surface of the object believed to contain the fingerprints. In all other respects, the third process is the same as that described in Example II.

EXAMPLE IV

It may sometimes be impossible or dangerous to charge the object bearing the fingerprints to a high voltage or the object may not be susceptible to holding an electric charge and in this event a fourth process may be used. In this process the object bearing the fingerprint is immersed in a bath of liquid dielectric containing finely divided carbon in suspension, the batch containing two electrodes between which an electric field is established into which the object is introduced. The electric field causes the carbon particles to migrate and by appropriately positioning the object in the electric field, the particles can be made to adhere to the object and produce a pattern thereon corresponding to the fingerprint.

After producing this pattern, the electric field can be removed and the object withdrawn and the pattern fixed thereon, or lifted therefrom as previously described, using adhesive backed sheet material or clear varnish and the like.

I claim:

1. A method of rendering visible a fingerprint contained on an area comprising the steps of:
   (1) covering the area with a flexible sheet which is sensitive to skin oil secretions and capable of retaining an electrostatic charge,
   (2) firmly pressing the sheet into contact with the said area,
   (3) separating the sheet from the said area,
   (4) subjecting the sheet to an electrostatic field so as to impart an electrostatic charge thereover which will be less in areas bearing skin secretions of the fingerprint,
   (5) removing the electrostatic field, and
   (6) applying to the sheet a finely divided particulate material so that the particles adhere to strongly charged regions of the sheet but areas having little or no charge are substantially uncoated by the particles thereby to produce a pattern corresponding to the fingerprint.

2. A method as set fourth in claim 1 wherein a transparent protective layer is applied over the pattern of particles defining the fingerprint.

3. A method as set fourth in claim 2 wherein the transparent layer is a sheet of adhesive backed transparent material and the pattern is lifted by peeling the transparent material from off the said surface after it has been pressed into contact therewith.

4. A method as set fourth in claim 1 further comprising the step of:
   forming over the pattern of particles defining the fingerprint a transparent protective layer by spraying thereon material which will form the protective layer.

5. A method of rendering visible a fingerprint contained on an area of a member which will at least temporarily support an electric charge comprises the steps of:
   (1) subjecting at least the said area of the member to an electrostatic field so as to impart a charge thereto, and
   (2) applying finely divided particulate material to the area which has been electrically charged, and forming thereon a pattern of the particulate material corresponding to any fingerprint thereon.

6. A method as set forth in claim 5 where the step of applying the particulate material to the said area comprises the steps of:
   (1) immersing the said area in a bath containing a suspension of the particulate material in a liquid dielectric and causing a migration of the particulate material to the said area under the action of an electric field,
   (2) removing the said area from the bath, and
   (3) permitting the liquid to evaporate and leave the pattern of particulate material behind on the said area.

7. A method as set forth in claim 6 further comprising the step of:
   applying over the pattern of particulate material defining the fingerprint a transparent protective layer.

8. A method of rendering visible a fingerprint contained on an area of a member which is portable and will support at least temporarily an electric charge, comprises the steps of:
   (1) immersing the member in a suspension of a finely divided particulate material in a dielectric liquid
   (2) establishing an electric field in the dielectric liquid thereby causing the particulate material in the suspension to migrate in the direction of the immersed member, the particulate material forming visible pattern thereon corresponding to any fingerprints on the said area, and
   (3) removing the member from the dielectric liquid.

9. A method as set forth in claim 8 further comprising the steps of:
   (1) permitting liquid adhereing to the said member to evaporate, and
   (2) applying over the pattern of particulate material defining the fingerprint a transparent protective layer.

* * * * *